United States Patent [19]

Gerster

[11] Patent Number: 5,367,076

[45] Date of Patent: Nov. 22, 1994

[54] PROCESS FOR IMIDAZO[4,5-C]QUINOLIN-4-AMINES

[75] Inventor: John F. Gerster, St. Paul, Minn.

[73] Assignee: Minnesota Mining and Manufacturing Company, St. Paul, Minn.

[21] Appl. No.: 879,149

[22] Filed: Apr. 30, 1992

Related U.S. Application Data

[63] Continuation of Ser. No. 593,078, Oct. 5, 1990, abandoned.

[51] Int. Cl.$^5$ ............... C07D 471/02; C07D 471/04
[52] U.S. Cl. ........................... 546/82; 546/159
[58] Field of Search .......................... 546/82

[56] References Cited

U.S. PATENT DOCUMENTS

| | | | |
|---|---|---|---|
| 4,689,338 | 8/1987 | Gerster | 514/293 |
| 4,929,624 | 5/1990 | Gerster et al. | 514/293 |
| 4,988,815 | 1/1991 | André et al. | 546/159 |

OTHER PUBLICATIONS

Wade Organic Chemistry pp. 456–457, Prentice–Hall Inc. Publishers 1987.
Mar., Advanced Organic Chemistry, Second Edition pp. 392–393, McGraw–Hill Publishers QD251 M2 1977 C5.
Solekhova, Khim. Get. Soed., 2, 229 (Feb. 1976).
Hamana et al., Chem. Pharm. Bull., 84, 35 (1964).

Primary Examiner—Alan L. Rotman
Attorney, Agent, or Firm—Gary L. Griswold; Walter N. Kirn; Douglas E. Reedich

[57] ABSTRACT

A process is disclosed for preparing 1-substituted-1H-imidazo[4,5-c]quinolin-4-amines. The process involves reacting a 1-substituted-1H-imidazo[4,5-c]quinoline-5-oxide with an acylating agent and reacting the product thereof with an aminating agent.

6 Claims, No Drawings

PROCESS FOR IMIDAZO[4,5-C]QUINOLIN-4-AMINES

This is a continuation of application Ser. No. 07/593,078 filed Oct. 5, 1990 now abandoned.

BACKGROUND OF THE INVENTION

1. Field of the Invention

This invention relates to processes for preparing 1H-imidazo[4,5-c]quinolines. In another aspect this invention relates to processes for preparing 1-substituted-1H-imidazo[4,5-c]quinolin-4-amines.

2. Description of the Related Art

The synthesis of 1H-imidazo[4,5-c]quinolin-4-amines has been described in U.S. Pat. Nos. 4,689,338 (Gerster) and 4,929,624 (Gerster et al.). The methods described therein involve the step of heating the 4-chloro compound in the presence of ammonium hydroxide or ammonia under pressure (e.g., in a sealed reactor) to afford the 4-amino compound.

Khim. Geterosiklicheskikh Soedinenii 1976, 2, 229 (Solekhova et al.) describes the amination of pyridine N-oxide and quinoline N-oxide at the 2-position with ammonia and some ammonia salts in the presence of p-toluenesulfonyl chloride. Similarly, Chem. Pharm. Bull. (Tokyo) 1984, 1, 35 (Hamana et al.) describes the reaction between quinoline 1-oxide and various amines in the presence of an acylating agent.

SUMMARY OF THE INVENTION

This invention provides a process for preparing a compound of Formula I

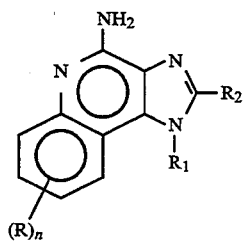

wherein
$R_1$ is straight chain or branched chain alkyl of one to about 10 carbon atoms; straight chain or branched chain alkenyl of 3 to about 10 carbon atoms wherein the olefinic unsaturation in the alkenyl group is at least one carbon atom removed from the 1-nitrogen; substituted straight chain or branched chain alkenyl of 3 to about 10 carbon atoms wherein the olefinic unsaturation is at least one carbon atom removed from the 1-nitrogen, wherein the substituent is selected from the group consisting of lower alkyl, cycloalkyl of 3 to about 6 carbon atoms, and cycloalkyl of 3 to about 6 carbon atoms substituted by lower alkyl; and substituted straight chain or branched chain alkyl of one to about 10 carbon atoms, wherein the substituent is selected from the group consisting of lower alkyl, cycloalkyl of 3 to about 6 carbon atoms, and cycloalkyl of 3 to about 6 carbon atoms substituted by lower alkyl;

$R_2$ is selected from the group consisting of hydrogen, straight chain or branched chain alkyl containing one to about eight carbon atoms; benzyl, (phenyl)ethyl and phenyl, the benzyl, (phenyl)ethyl or phenyl substituent being optionally substituted on the benzene ring by one or two moieties independently selected from the group consisting of lower alkyl, lower alkoxy, and halogen, with the proviso that when the benzene ring is substituted by two such moieties, then the moieties together contain no more than 6 carbon atoms;

each R is independently selected from the group consisting of lower alkoxy, halogen, and lower alkyl, and n is an integer from zero to 2, with the proviso that if n is 2, then said R groups together contain no more than 6 carbon atoms; or a pharmaceutically acceptable acid addition salt thereof, which process comprises the steps of:

(i) providing a compound of Formula II

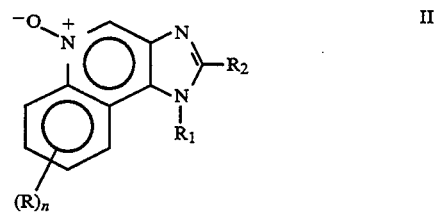

wherein R, n, $R_1$, and $R_2$ are as defined above;

(ii) reacting the compound of Formula II with an acylating agent; and (iii) reacting the product of step (ii) with an aminating agent in an inert solvent to provide a compound of Formula I; and (iv) isolating the compound of Formula I or a pharmaceutically acceptable acid addition salt thereof.

This invention provides a process by which an N-oxide of Formula II can be aminated without the use of the high pressure conditions used in previous syntheses of imidazo[4,5-c]quinolin-4-amines, and without isolation of an intermediate. The process of this invention is therefore more convenient than the previous syntheses. Moreover, yield and purity of the product of Formula I is improved by the process of this invention.

DETAILED DESCRIPTION OF THE INVENTION

For the purpose of the instant specification and claims, the term "lower" when used in connection with "alkyl" or "alkoxy" designates straight chain or branched chain groups containing 1 to about 4 carbon atoms.

The process of this invention is illustrated in the Reaction Scheme below, wherein R, n, $R_1$, and $R_2$ are as defined above.

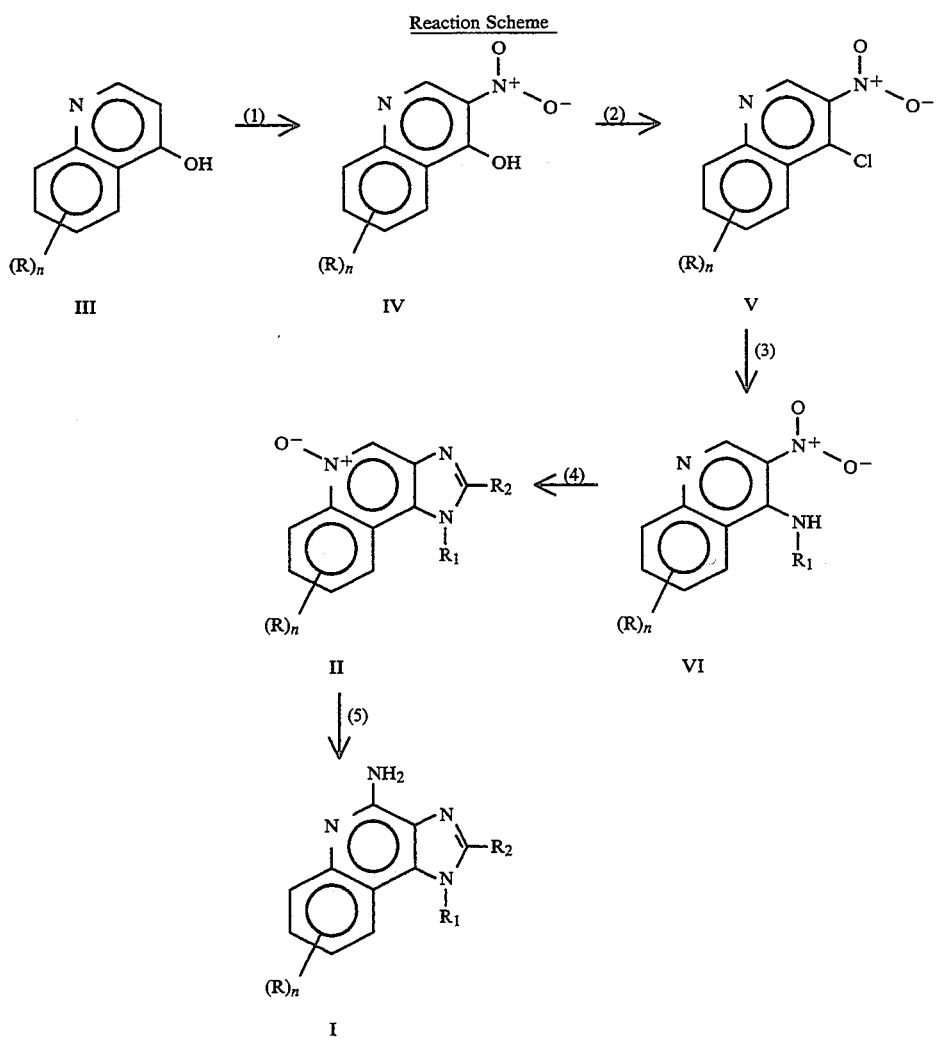

Reaction Scheme

The Reaction Scheme begins with a 4-hydroxyquinoline of Formula III. Many 4-hydroxyquinolines of Formula III are commercially available. The others are known and/or can be prepared readily by those skilled in the art. Step 1 involves nitration of a 4-hydroxyquinoline to provide a 3-nitro-4-hydroxyquinoline of Formula IV. Conventional conditions for such reactions are well known. Preferred conditions in the instance where n is zero, which afford a product of Formula IV in superior yield compared with conditions used in the prior art, involve heating at about 125° C.-130° C. in propionic acid in the presence of nitric acid. Preferred conditions in other instances will depend upon the particular 4-hydroxyquinoline used in step 1, and those skilled in the art will be able to select suitable conditions.

In step 2, a 3-nitro-4-hydroxyquinoline is chlorinated at the 4-position to provide a 3-nitro-4-chloroquinoline of Formula V. Some compounds of Formula V are known and disclosed, e.g., in U.S. Pat. No. 3,700,674 (Diehl et al.) and references cited therein, and U.S. Pat. No. 4,689,338 (Gerster), both patents being incorporated herein by reference. The others can be prepared as shown in step 2. Step 2 can be carried out by reacting a compound of Formula IV in an inert solvent (e.g., methylene chloride) with a chlorinating agent (e.g., phosphorus oxychloride). Preferred conditions involve chlorination in methylene chloride with a Vilsmeier reagent prepared from thionyl chloride and N,N-dimethylformamide. In such a reaction, the compound of Formula IV is suspended in methylene chloride, and a slight molar excess of thionyl chloride and N,N-dimethylformamide is added to the suspension. Heating to reflux facilitates the chlorination.

Step 3 involves reacting a compound of Formula V in an inert solvent with an amine of the formula $R_1NH_2$ to provide a compound of Formula VI. Some compounds of Formula VI are disclosed in U.S. Pat. No. 4,689,338 (Gerster). The others can be prepared as shown in step 3. The reaction of step 3 is preferably carried out in the presence of a tertiary amine catalyst (such as triethylamine), and it is preferred to run the reaction without isolation of the chloro compound from step 2.

Step 4 involves: (i) reduction of the nitro group of the compound of Formula VI; (ii) reaction of the resulting 3-amino compound with a carboxylic acid or an equivalent thereof in order to provide a cyclized imidazo[4,5-c]quinoline; and (iii) oxidizing the quinoline nitrogen to provide the N-oxide of Formula II. Some compounds of Formula II are disclosed in U.S. Pat. No. 4,689,338 (Gerster). The others can be prepared as shown in step 4.

The reduction in step (4) is preferably carried out using a conventional heterogeneous hydrogenation catalyst such as platinum on carbon. The reduction can be carried out conveniently on a Paar apparatus in an inert solvent such as toluene, ethyl acetate, or a lower alkanol. In part (ii) of step 4, a 3-amino compound is reacted with (a) a 1,1-dialkoxyalkyl alkanoate such as diethoxymethyl acetate, or (b) a carboxylic acid that will introduce the desired $R_2$ group, or (c) a trialkyl ortho ester of the formula $R_2C(Oalkyl)_3$, wherein "alkyl" is an alkyl group containing 1 to about 4 carbon atoms, or (d) a combination of such a carboxylic acid with such a trialkyl ortho ester to provide an imidazo[4,5-c]quinoline. The reaction can be carried out by heating, e.g., at about 130° C., in the presence of an acid, preferably an alkanoic acid having one more carbon atom than $R_2$.

Part (iii) of step (4) provides an intermediate of Formula II. The quinoline nitrogen is oxidized with a conventional oxidizing agent that is capable of forming N-oxides. Preferred oxidizing agents include peroxyacids (such as peroxyacetic acid) and hydrogen peroxide. Preferred conditions involve mild heating (e.g., at about 50° C.–60° C.) in an ethanolic solution of peroxyacetic acid.

A 1H-imidazo[4,5-c]quinolin-4-amine is prepared in step (5) of the Reaction Scheme. Step (5) involves (i) reacting a compound of Formula II with an acylating agent; (ii) reacting the product with an aminating agent; and (iii) isolating the compound of Formula I. Part (i) of step (5) involves reacting an N-oxide with an acylating agent. Suitable acylating agents include alkyl- or arylsulfonyl chlorides (e.g., benzenesulfonyl chloride, methanesulfonyl chloride, p-toluenesulfonyl chloride). Arylsulfonyl chlorides are preferred. p-Toluenesulfonyl chloride is most preferred. Part (ii) of step (5) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, and ammonium phosphate). Ammonium hydroxide is preferred. The reaction of step (5) is preferably carried out by dissolving the N-oxide from Formula II in an inert solvent such as methylene chloride, adding the aminating agent to the solution, and then adding the acylating agent. Preferred conditions involve cooling to about 0° C. to about 5° C. during the addition of the acylating agent. Heating or cooling can be used to control the rate of the reaction. The product compound of Formula I can be isolated by the conventional means disclosed in U.S. Pat. No. 4,689,338 (Gerster), such as, for example, removal of the solvent and recrystallization from an appropriate solvent (e.g., N,N-dimethylformamide) or solvent mixture, or by dissolution in an appropriate solvent (e.g., methanol) and re-precipitation by addition of a second solvent in which the compound is insoluble.

The compounds of Formula I can be used in the form of acid addition salts such as hydrochlorides, dihydrogen sulfates, trihydrogen phosphates, hydrogen nitrates, methane sulfonates and salts of other pharmaceutically acceptable acids. Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid or an organic acid such as methanesulfonic acid in a polar solvent. Isolation of the salt is facilitated by the addition of a solvent in which the salt is insoluble (e.g., diethyl ether).

The 1H-imidazo[4,5-c]quinolin-4-amines prepared by the process of this invention are disclosed in U.S. Pat. Nos. 4,689,338 (Gerster) and 4,929,624 (Gerster et al.) as antiviral agents. The process as described above is illustrated in the Example below for the synthesis of 1-(2-methylpropyl)-1H-imidazo[4,5-c]quinolin-4-amine. The process affords the final product in a 40% overall yield from 4-hydroxyquinoline.

In the following Example, all reactions were run with stirring under an atmosphere of dry nitrogen unless otherwise indicated. The particular materials and amounts thereof recited in the Example, as well as other conditions and details, should not be construed to unduly limit the invention.

EXAMPLE

The preparation of 1-(2-methylpropyl)-1H-imidazo[4,5-c]quinolin-4-amine.

Part A

4-Hydroxyquinoline (26.2 g, 0.18 mol) was added to propionic acid (250 mL) and the solution was heated to about 125° C. Nitric acid (16.0 mL of a 70 percent aqueous solution, 0.36 mol) was added dropwise with stirring. When the addition was complete, the mixture was stirred at about 125° C. for 10 minutes, then allowed to cool to room temperature. The mixture was diluted with ethanol. The precipitated solid was filtered, washed sequentially with ethanol, water, and ethanol, and dried to afford 3-nitro-4-hydroxyquinoline (27.7 g, 86%) as a light yellow powder.

Part B

The compound 3-nitro-4-hydroxyquinoline (19.0 g, 0.10 mol) was suspended in dichloromethane (200 mL). Thionyl chloride (8.1 mL, 0.11 mol) and N,N-dimethylformamide (8.5 mL, 0.11 mol) were added. The reaction mixture was then heated for 3.5 hours at reflux, during which time a small amount of solid precipitated. The reaction mixture was then cooled to −15° C. and a solution of isobutylamine (15.1 mL, 0.15 mol), and triethylamine (20.9 mL, 0.15 mol) in dichloromethane (100 mL) was added in a slow stream with vigorous swirling. During the addition the temperature of the reaction mixture rose to 20° C. The resulting solution was heated at reflux for 30 minutes, cooled, and the solvent was removed at reduced pressure to afford a yellow solid product. The product was slurried in water, filtered, washed with water, and dried partially. The partially dried product was then slurried in ethanol (75 mL), filtered, washed successively with a small amount of ethanol and a small amount of diethyl ether, and dried at reduced pressure to afford a yellow crystalline solid product. A second crop of product was obtained by evaporating the ethanol filtrate. The total amount of N-(2-methylpropyl)-3-nitro-4-quinolinamine was 23.3 g.

Part C

N-(2-methylpropyl)-3-nitro-4-quinolinamine (61.3 g, 0.25 mol) was placed in a Paar apparatus along with 5% Pt/C (1.5 g), magnesium sulfate (60 g), ethyl acetate (750 mL), and formic acid (400 mL). The mixture was placed under a hydrogen atmosphere (about 50 psi) and hydrogenated. The catalyst was removed by filtration and the solvent was evaporated to afford the crude product. The crude product was dissolved in 98% formic acid (400 mL) and refluxed for 1 hour. The resulting solution was evaporated to dryness and the resulting solid was dissolved in ethanol (400 mL). Peroxyacetic acid (63 mL of an acetic acid solution containing 32% peroxyacetic acid based on the total weight of the solution, 0.3 mol) was added and the solution was heated at 56° C. for about 0.5 hour. The solution was then cooled and the solvents were removed at reduced pressure. The residue was then co-evaporated with heptane (3×300 mL) to afford a solid. The solid was dissolved in dichloromethane (550 mL) in a Hirsch flask and ammonium hydroxide (125 mL of an aqueous solution containing 28% ammonia by weight based on the total weight of the solution) was added. The resulting mixture was cooled to 0° C. and a solution of p-toluenesulfonyl chloride in dichloromethane (52.4 g, 0.275 mol, in 125 mL dichloromethane) was added dropwise over 20 min. The temperature was maintained in the range of 0° C. to about 5° C. during the addition. After the addition, the reaction mixture was stirred at room temperature for 2 hours. The precipitate was filtered, slurried in ethanol, filtered again, and washed sequentially with ethanol and ether to afford solid 1-(2-methylpropyl)-1H-imidazo[4,5-c]quinolin-4-amine (45.6 g, 76% crude yield). A 10 g sample of the crude product was dissolved in concentrated hydrochloric acid (25 mL) and the solution was treated with sodium dithionite (3.3 g). The solution was then heated in a steam bath for 15 minutes and diluted with water (75 mL). The product precipitated and was filtered. The solid was then dissolved in a minimum amount of methanol and precipitated by addition of a solution of potassium hydroxide in methanol. The precipitate was filtered and washed with methanol to afford 6.6 g (50% purified yield) of 1-(2-methylpropyl)-1H-imidazo[4,5-c]quinolin-4-amine with melting point and spectral properties identical to those of an authentic sample.

I claim:

1. A process for preparing a compound of the formula:

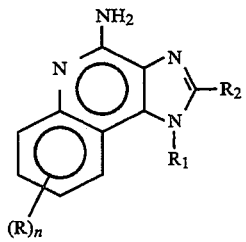

wherein $R_1$ is straight chain or branched chain alkyl of one to about 10 carbon atoms; straight chain or branched chain alkenyl of 3 to about 10 carbon atoms wherein the olefinic unsaturation in the alkenyl group is at least one carbon atom removed from the 1-nitrogen; substituted straight chain or branched chain alkenyl of 3 to about 10 carbon atoms wherein the olefinic unsaturation is at least one carbon atom removed from the 1-nitrogen, wherein the substituent is selected from the group consisting of lower alkyl, cycloalkyl of 3 to about 6 carbon atoms, and cycloalkyl of 3 to about 6 carbon atoms substituted by lower alkyl; and substituted straight chain or branched chain alkyl of one to about 10 carbon atoms, wherein the substituent is selected from the group consisting of lower alkyl, cycloalkyl of 3 to about 6 carbon atoms, and cycloalkyl of 3 to about 6 carbon atoms substituted by lower alkyl;

$R_2$ is selected from the group consisting of hydrogen, straight chain or branched chain alkyl containing one to about eight carbon atoms; benzyl, (phenyl)ethyl and phenyl, the benzyl, (phenyl)ethyl or phenyl substituent being optionally substituted on the benzene ring by one or two moieties independently selected from the group consisting of lower alkyl, lower alkoxy, and halogen, with the proviso that when the benzene ring is substituted by two such moieties, then the moieties together contain no more than 6 carbon atoms;

each R is independently selected from the group consisting of lower alkoxy, halogen, and lower alkyl, and n is an integer from zero to 2, with the proviso that if n is 2, then said R groups together contain no more than 6 carbon atoms; or a pharmaceutically acceptable acid addition salt thereof, which process comprises the steps of:

(i) providing a compound of Formula II

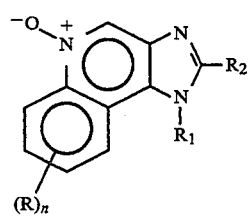

wherein R, n, $R_1$, and $R_2$ are as defined above;

(ii) reacting the compound of Formula II with an alkylsulfonyl chloride or an arylsulfonyl chloride; and (iii) reacting the product of step (ii) with an aminating agent in an inert solvent to provide a compound of Formula I; and (iv) isolating the compound of Formula I or a pharmaceutically acceptable acid addition salt thereof.

2. A process according to claim 1 wherein in step (ii) the product of Formula II is reacted with an arylsulfonyl chloride.

3. A process according to claim 2, wherein the arylsulfonyl chloride is p-toluenesulfonyl chloride.

4. A process according to claim 1, wherein the aminating agent is ammonia or an ammonium salt.

5. A process according to claim 1, wherein the aminating agent is ammonium hydroxide.

6. A process according to claim 1 wherein the compound is 1-(2-methylpropyl)-1H-imidazo[4,5-c]quinolin-4-amine.

* * * * *